United States Patent [19]

Benecke et al.

[11] 4,427,694

[45] Jan. 24, 1984

[54] SESAMIN AS A PSYCHOTROPIC AGENT

[75] Inventors: Herman P. Benecke; Bob E. Sherwood, both of Columbus, Ohio

[73] Assignee: The Vinoxen Company, Inc., Stamford, Conn.

[21] Appl. No.: 387,638

[22] Filed: Jun. 11, 1982

[51] Int. Cl.$^3$ ............................................. A61K 31/36
[52] U.S. Cl. .................................................... 424/282
[58] Field of Search ......................................... 424/282

[56] References Cited
PUBLICATIONS

Chem. Abst., vol. 78 (1973) 68239a.

Primary Examiner—Stanley J. Friedman
Attorney, Agent, or Firm—Millen & White

[57] ABSTRACT

A method for producing a psychotropic response, especially for alleviating the symptoms of alcohol withdrawal, comprises administering to a human or animal subject in need thereof a psychotropically effective non-toxic amount of sesamin. A composition for use in the present method is provided.

16 Claims, No Drawings

SESAMIN AS A PSYCHOTROPIC AGENT

BACKGROUND OF THE INVENTION

This invention relates to a method for producing a psychotropic response involving administration of sesamin. In a composition of matter aspect, the invention also relates to a pharmaceutical composition suitable for use with the foregoing method.

Sesamin is a naturally occurring compound found in sesame oil and in the bark and fruit of certain plant species. It has been used as a synergist for insecticides, but heretofore, there has been no suggestion of its use as a psychotropic agent.

OBJECTS OF THE INVENTION

One object of the present invention is to provide a method for producing a psychotropic response, particularly at least one of an antidepressant, tranquilizing or anticonvulsant response, or alleviation of the symptoms of alcohol intoxication or alcohol or tobacco withdrawal.

Another object of the present invention is to provide a pharmaceutical composition for use in the foregoing method.

Upon further study of the specification and appended claims, further objects and advantages of this invention will become apparent to those skilled in the art.

SUMMARY OF THE INVENTION

In a method aspect, the present invention provides a method for producing a psychotropic response in a human or animal subject, comprising administering to said subject a psychotropically effective non-toxic amount of sesamin.

In a composition aspect, the present invention provides a psychotropic composition comprising a non-toxic amount effective for producing a psychotropic response in a human or animal subject of sesamin, and a pharmaceutically acceptable carrier.

DETAILED DISCUSSION

Sesamin or 2,6-bis-(3,4-methylenedioxyphenyl)-3,7-dioxibicyclo[3.3.0]octane has the empirical formula $C_{20}H_{18}O_6$, and has the formula

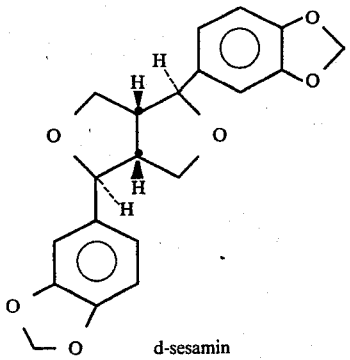

d-sesamin

The formula shows the d(+)-sesamin stereoisomer, but use of the racemic dl-form is also included within the scope of the invention.

Isolation of sesamin from sesame oil may be effected by the process of Bertram et al., *Biochem. Z.*, 197, 1 (1928). The dl-form may be synthesized according to the processes of Beroza et al., *J. Am. Chem. Soc.*, 78, 1242, (1956) or Freudenberg, *Naturwiss.*, 43, 16 (1956). The dl-form is also known as fagarol, and may be isolated from the bark of various fagara species. The d-form may be prepared by effecting a conventional resolution of a convenient synthetic precursor such as the tetrahydroxy intermediate in the Beroza et al. scheme.

Sesamin may also be prepared as a concentrate from sesame oil in which it is present in amounts of about 0.4–1.1%. For example, both the unsaponifiable fraction from saponification of sesami oil and the early fractions from molecular distillation of sesame oil contain higher levels of sesamin than the natural oil. See, e.g., Budowski et al., *Chem. Revs.*, 48, 125–151 (1951); Embree, *Chem. Revs.*, 29, 317–332 (1941). Further concentration and/or purification may be effected by chromatography, selective extraction or other conventional techniques. Such concentrates can be used in place of pure, crystalline sesamin in the method and composition of the present invention.

Sesamin, either as the d-form or the dl-form, has now been found to possess psychotropic activity, i.e., administration of appropriate dosages to a human or animal subject elicits a psychotropic response. By psychotropic response is meant any one of a variety of therapeutic effects on the central nervous system, which include but are not limited to tranquilizing, antidepressant or anticonvulsant effects, as well as alleviation of the symptoms of alcohol intoxication and/or alcohol or tobacco withdrawal. A preferred method of use is in alleviating alcohol intoxication or withdrawal symptoms, wherein administration of sesamin is particularly effective.

While the reasons for the effectiveness of any psychotropic agent are often unclear, it has been found that administration of sesamin to humans and animals has a calming, anxiety-reducing effect which is especially helpful for those who are experiencing alcohol or tobacco withdrawal symptoms. In addition, other symptoms associated with alcohol withdrawal are reduced in severity upon administration of an effective amount of sesamin in an appropriate dosage form.

Evaluation of the efficacy of sesamin in alleviating alcohol withdrawal symptoms is shown by the use of a reliable primate model system, wherein a Cynomolgus monkey is addicted to alcohol over a period of a few weeks, the alcohol is withdrawn and the presence and severity of specific symptoms associated with withdrawal are first evaluated during administration of a placebo, after which the animal is re-addicted to alcohol and the same symptoms are evaluated while sesamin is administered during a withdrawal period of the same duration. A comparison of the total symptom score between the placebo withdrawal and the drug withdrawal period is a reliable measure of the efficacy of a drug in alleviating withdrawal symptoms, as disclosed in U.S. Ser. No. 106,129, filed Dec. 21, 1979. In that application, the primate model was used to evaluate a drug which was also clinically tested in a large number of subjects, and the primate model was shown to give results which were consistent with the clinical results.

Administration of sesamin for the purpose of eliciting a psychotropic response is advantageously effected in daily amounts of about 0.1–150 mg per kg of patient body weight, preferably about 1–50 mg/kg. For the particular purpose of alleviating alcohol withdrawal symptoms, the daily dosage range is about 1–20 mg/kg, preferably about 2–10 mg/kg. The dose can be administered singly or as divided dosages throughout the day.

Administration of sesamin in appropriate dosages to a human or animal, especially a mammal, suffering from nervousness and/or anxiety produces a calming, tranquilizing response. An effective daily tranquilizing dosage of sesamin can generally range from about 10 mg to about 2 g, depending on the person or animal treated and the severity of the symptoms.

Administration of sesamin in appropriate dosages to a human or animal, especially a mammal, suffering from convulsions produces an anticonvulsant response. An effective daily anticonvulsant dosage of sesamin can generally range from about 10 mg to about 2 g, depending on the person or animal treated and the severity of the symptoms.

Administration of sesamin in appropriate dosages to a human or animal, especially a mammal, suffering from depression produces an antidepressant response. An effective daily antidepressant dosage of sesamin can generally range from about 10 mg to about 2 g, depending on the person or animal treated and the severity of the symptoms.

Administration of sesamin in appropriate dosages to a human suffering from tobacco withdrawal symptoms alleviates the symptoms. An effective daily therapeutic dosage of sesamin for alleviation of tobacco withdrawal symptoms can generally range from about 10 mg to about 2 g, depending on the person treated and the severity of the symptoms.

Sesamin may be provided in pure or substantially pure crystalline form for use in the method and composition of this invention. Alteratively, sesamin may be used in the form of a concentrate or isolate from one or more of the extraction, separation and/or purification procedures described above. Advantageously, concentrates and/or fractions having a sesamin content higher than natural sesame oil, e.g., about 1.2–10% by weight, preferably 10–40%, more preferably 40–70%, and most preferably at least about 70%, may be used.

It will ordinarily be impractical to use sesame oil itself as the sesamin-containing composition since the 0.4–1.1 weight % sesamin content of sesame oil could entail administration of unacceptably large amounts in order to provide enough sesamin for effective treatment. Nevertheless, the use of sesame oil as the sesamin source is not excluded.

The compounds of this invention can be employed in mixture with conventional excipients, i.e., pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, and the like. The pharmaceutical preparations can be sterilized and if desired mixed with auxiliary agents, e.g., lubricants, preservatives, stabilizers, wetting agents, emulsifiers, salts for influencing osmotic pressure, buffers coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or wheat starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, and the like.

Generally, the compounds of this invention are dispensed in unit dosage form comprising about 1 mg–1 g of a pharmaceutical carrier per each unit dosage and the amount of sesamin per each unit dosage is about 0.5–500 mg.

A preferred mode of administration is by oral administration of tablets and/or capsules containing sesamin and one or more inert binders and/or excipients. The individual dosage units are advantageously tablets containing about 50–500 mg of sesamin.

For a patient suffering from alcohol withdrawal symptoms, it is advantageous for the patient to take one such tablet four times per day for the first three days after withdrawal, desirably when the patient is sober, and to take one tablet two or three times per day for the next four days. Such a dosage is generally sufficient to eliminate or reduce the desire or need for alcohol and to alleviate any withdrawal symptoms which the patient might otherwise suffer. If the desire or need for alcohol recurs, the patient may be given an additional supply of the sesamin tablets, and directed to take a capsule if he or she feels any desire or need for alcohol or any recurrence of withdrawal symptoms.

A combination of injections and tablets or other oral dosage forms may also be used where indicated. In addition, the foregoing dosage forms may be used to reduce the severity of alcohol intoxication and/or to prevent or minimize alcohol intoxication prior to consumption of alcoholic beverages.

Similar dosage forms may be used for eliciting the broad range of psychotropic responses indicated hereiabove. The particular dosages will generally be within the broad ranges given above, but will vary in relation to the severity of the clinical symptoms and the type of response to be elicited, in a manner which will be familiar to the skilled clinical practitioner.

Without further elaboration, it is believed that one skilled in the art can, using the preceding description, utilize the present invention to its fullest extent. The following preferred specific embodiments are, therefore, to be construed as merely illustrative, and not limitative or the remainder of the disclosure in any way whatsoever.

EXAMPLE 1

Tablet Formulation

A tablet suitable for administration according to the method of the invention is prepared as follows. Each dosage unit is designed for administration to a patient weighing about 80 kg, and administration of four such tablets on each of the first three days of alcohol withdrawal and two or three tablets for each of the next four days is envisioned. Suitable variation and dosage as a function of patient weight is indicated.

|  | Weight |
| --- | --- |
| (a) d(+)-sesamin | 100 g |
| (b) Wheat starch | 13 g |
| (c) Lactose | 38 g |
| (d) Magnesium stearate | 3 g |

A granulation obtained upon mixing lactose with a portion of the starch and granulated starch paste made from the remainder of the starch is dried, screened and mixed with the sesamin and the magnesium stearate. The mixture is compressed into 1,000 tablets weighing about 154 mg each. It will be understood that a dragee or a capsule may be used in place of a tablet, and it may be prepared by conventional techniques.

EXAMPLE 2

Sesamin was tested for its efficacy in alleviating alcohol withdrawal symptoms in an alcohol-addicted Cynomolgus monkey, using water as a placebo. For each test, a monkey was addicted to ethyl alcohol by infusion of 5 ml/hr for 28 days of a solution ranging between 15 and 30% ethyl alcohol in normal saline. The ethyl alcohol solutions was administered via an indwelling silastic catheter implanted into the jugular vein. The presence of and severity of withdrawal was evaluated according to the presence and severity of specific symptoms, which are known to be exhibited by monkeys upon removal of alcohol in a dependent animal. Evaluation was based on a scale of 0: symptom not present, 1: mild presence of symptom, 2: moderate presence of symptom, and 3: severe presence of symptom. The symptoms evaluated were: generalized tremors, muscle fasciculations, elicited hyperreflexia, spasticity, rigidity, spontaneous hyperreflexia, fright, salivation, mydriasis, retching-vomiting, convulsive poses, convulsions, aggression, nervousness, excitability, and evoked threat.

During the 5-day placebo withdrawal period, which immediately followed the 28-day addiction period, the monkey received 5 ml of water injected into orange slices. The withdrawal symptoms were evaluated daily during this period. At the conclusion of the placebo withdrawal period, the animal was re-addicted to the ethyl alcohol over a 14-day period as described above. This was immediately followed by a 5-day drug withdrawal period. During this period, the animal received a daily dose of 14.3 mg of sesamin dissolved in 5 ml of triolein and injected into orange slices, and the daily withdrawal symptoms were each evaluated using the above rating system. The lower the score, the less severe the symptoms and the more efficacious the therapeutic effect compared to placebo administration. The total symptom score was 46 for placebo and 30 for sesamin, representing a reduction (placebo-drug/-placebo×100) of 35%. A percent reduction higher than 20% is considered significant.

It can be seen from these data that sesamin has been shown to be effective for alleviation of the symptoms of alcohol withdrawal in a reliable primate odel. Sesamin was most effective in reducing nervousness, aggression, fright, threat and generalized tremors.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make varius changes and modifications of the invention to adapt it to various usages and conditions.

What is claimed is:

1. A method for producing a psychotropic response in a human or animal subject suffering from a condition for which a psychotropic response would be therapeutic, comprising administering to said subject a psychotropically effective non-toxic amount of sesamin.

2. The method of claim 1, wherein said subject is suffering from anxiety and said response is a tranquilizing effect.

3. The method of claim 1, wherein said subject is suffering from depression and said response is an antidepressant effect.

4. The method of claim 1, wherein said subject is suffering from convulsions and said response is an anticonvulsant effect.

5. The method of claim 1, wherein said subject is suffering from symptoms of tobacco withdrawal and said response is alleviation of tobacco withdrawal symptoms.

6. The method of claim 1, wherein said effective amount is about 0.1–150 mg per kg of subject body weight per day.

7. The method of claim 6, wherein said amount is about 1–50 mg/kg/day.

8. The method of claim 1, wherein sesamin is administered orally.

9. A method for alleviating symptoms of alcohol withdrawal or alcohol intoxication in a human or animal subject suffering from said symptoms, comprising administering to said subject a non-toxic amount effective to alleviate said symptoms of sesamin.

10. The method of claim 9, wherein said subject is suffering from symptoms of alcohol withdrawal and said response is alleviation of alcohol withdrawal symptoms.

11. The method of claim 9, wherein said subject is suffering from symptoms of alcohol intoxication and said response is alleviation of the symptoms of alcohol intoxication.

12. The method of claim 9, wherein said effective amount is about 1–20 mg per kg of subject body weight per day.

13. The method of claim 12, wherein said amount is about 2–10 mg/kg.

14. The method of claim 12, wherein sesamin is administered orally.

15. A psychotropic composition, consisting essentially of a non-toxic amount effective for producing a psychotropic response in a human or animal subject of sesamin; and a pharmaceutically acceptable carrier; wherein said composition is in unit dosage form as a tablet, dragee, capsule, ampoule, suppository or sterile injectable preparation.

16. The composition of claim 15, wherein said amount is an amount effective to alleviate symptoms of alcohol withdrawal or alcohol intoxication.

* * * * *